United States Patent [19]

Kablaoui

[11] 4,000,171

[45] Dec. 28, 1976

[54] PREPARATION OF CARBOXYLIC AND HYDROXAMIC ACIDS FROM INTERNAL NITROKETONES

[75] Inventor: Mahmoud S. Kablaoui, Wappingers Falls, N.Y.

[73] Assignee: Texaco Inc., New York, N.Y.

[22] Filed: June 23, 1975

[21] Appl. No.: 589,328

[52] U.S. Cl. .................. 260/413; 260/500.5 H; 260/540; 260/541; 260/597 R
[51] Int. Cl.$^2$ ............... C07C 51/00; C07C 53/22; C07C 53/12
[58] Field of Search ........ 260/413, 500.5 H, 526 R, 260/540, 593 R, 644 R, 541

[56] References Cited

UNITED STATES PATENTS

| | | | |
|---|---|---|---|
| 2,168,305 | 8/1939 | Lippincott | 260/500.5 H |
| 3,518,302 | 6/1970 | Ellis | 260/413 |
| 3,895,071 | 7/1975 | Kablaoui et al. | 260/593 R |

*Primary Examiner*—Winston A. Douglas
*Assistant Examiner*—P. E. Konopka
*Attorney, Agent, or Firm*—T. H. Whaley; C. G. Ries; George J. Darsa

[57] ABSTRACT

A method of simultaneously preparing a carboxylic acid and a hydroxamic acid which comprises contacting an ammonium, Group IA or Group IIA salt of an alkyl alphanitroketone with an acidic mineral acid salt in a carboxylic acid solvent.

16 Claims, No Drawings

PREPARATION OF CARBOXYLIC AND HYDROXAMIC ACIDS FROM INTERNAL NITROKETONES

BACKGROUND OF THE INVENTION

This invention relates to a novel method of preparing acids and particularly to the simultaneous preparation of carboxylic and hydroxamic acids from ammonium salts of nitroketones.

Carboxylic acids and hydroxamic acids can be prepared employing such methods as oxidizing the corresponding alcohol and by Grignard synthesis or by reacting a carboxylic acid with hydroxylamine hydrochloride. Many carboxylic acids and hydroxamic acids however were not readily available particularly those containing an odd number of carbon atoms and relatively expensive reactants are required to obtain the same.

A method has now been found whereby a wide range of carboxylic acids and hydroxamic acids can be prepared in high yields. The method provides a mixture of carboxylic acid and hydroxamic acid and the respective acids can be separated one from the other as more fully described below.

SUMMARY OF THE INVENTION

Broadly, this invention contemplates a method of preparing a carboxylic acid and a hydroxamic acid which comprises contacting an ammonium, Group IA or Group IIA metal salt of a nitroketone with an acidic mineral acid salt in the presence of a carboxylic acid solvent.

In accordance with this invention, the salt of the nitroketone converted to the carboxylic and hydroxamic acid corresponds to the formula:

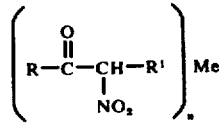

where R and R$^1$ are alkyl groups having from 1 to 25 carbon atoms and preferably from 1 to 20 carbon atoms and where Me is NH$_4$, a Group IA metal or a Group IIA metal and where n is 1 or 2. Illustrative of the Group IA metals are lithium, sodium and potassium and the Group IIA metals are represented by magnesium, calcium, strontium and barium. The preferred nitroketone salts are those of ammonium, sodium, calcium, and magnesium. It is essential to the method of this invention that the salts of internal nitroketones, that is, nonterminal alpha-nitroketones where the nitro and keto groups are on other than a terminal carbon atom be employed. Salts of terminal alpha-nitroketones, that is, 1-nitro-2-alkanones do not undergo the conversion to carboxylic and hydroxamic acids as herein more fully described.

The method contemplated by this invention is further explained by the following equation:

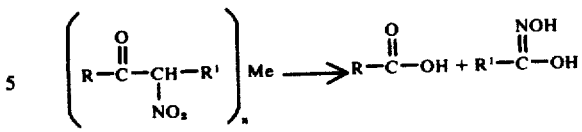

where R, R$^1$, n, and Me are as heretofore defined. From the equation it will be seen that the acids formed by the method are prepared from a reaction involving cleavage and hydrolysis wherein the salt of the alkyl nitroketone is converted to an alkanoic acid and an alkanohydroxamic acid.

Examples of suitable nitroketone salts used as starting material in the process of this invention include by illustration ammonium 2-nitro-3-butanone, ammonium 2-nitro-3-pentanone, ammonium 3-nitro-2-hexanone, ammonium 3-nitro-4-hexanone, ammonium 3-nitro-4-heptanone, ammonium 5-nitro-4-octanone, ammonium 4-nitro-5-decanone, ammonium 5-nitro-4-dodecanone, ammonium 8-nitro-7-heptadecanone, ammonium 7-nitro-8-heptadecanone, ammonium 8-nitro-9-hexadecanone and ammonium 3-nitro-4-eicosanone. Mixtures of ammonium salts of nitroketones can also be employed and provide as product mixtures of carboxylic and hydroxamic acids. The corresponding Group IA and IIA metal salts are also contemplated and are illustrated by sodium 2-nitro-3-butanone, potassium 3-nitro-4-hexanone, lithium 2-nitro-3-pentanone, magnesium 5-nitro-4-octanone, calcium 8-nitro-7-heptadecanone, barium 4-nitro-5-decanone, strontium 5-nitro-4-dodecanone as well as mixtures of Group IA or Group IIA salts of nitroketones. The half salts of the Group IIA metals are also contemplated by this method.

Illustrative of the acids prepared by the present method are the following carboxylic acids: acetic acid, propionic acid, n-butanoic acid, n-pentanoic acid, n-hexanoic acid, 4-methylhexanoic acid, 3,3-dimethylpentanoic acid, n-heptanoic acid, n-octanoic acid, n-decanoic acid and n-dodecanoic acid. Hydroxamic acids prepared by the method include for example acetohydroxamic acid, propanohydroxamic acid, butanohydroxamic acid, pentanohydroxamic acid, hexanohydroxamic acid, 4-methylhexanohydroxamic acid, n-heptanohydroxamic acid, n-octanohydroxamic acid, 3,3-dimethylpentanohydroxamic acid, n-decanohydroxamic acid and n-dodecanohydroxamic acid.

The salts of the nitroketones contemplated as starting materials above, can be prepared from an alkene corresponding to the formula:

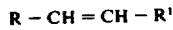

where R and R$^1$ are as heretofore defined, by contacting the alkene with dinitrogen tetroxide and oxygen at a temperature between about −40° and 20° C. employing a mole ratio of alkene to dinitrogen tetroxide to oxygen of between about 1:0.5:1 and 1:1.5:30 to form a nitroperoxy intermediate of the formula:

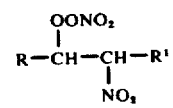

where R and R¹ are as heretofore defined. Thereafter the peroxy compound is contacted with a denitrating agent of the type known to the art at a temperature of between about −60° and 70° C. employing a mole ratio of denitrating agent to peroxy compound of about 1:1 to about 20:1 to form a non-terminal nitroketone of the formula:

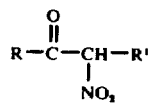

Alternatively, the alkene can be simultaneously contacted with dinitrogen tetroxide, oxygen and denitrating agent at a temperature of about 0° to 40° C. to directly prepare the above nitroketone. Representative denitrating agents include dimethylformamide, diethylformamide, dimethylacetamide, dimethylsulfoxide, diethylsulfoxide, tetramethylurea, tetraethylurea, hexamethylenephosphoramide, 1-methyl-2-pyrrolidinone, 1-ethyl-2-pyrrolidinone, 1-isobutyl-2-pyrrolidinone, and 1,3-dimethyl-2-pyrrolidinone. The reaction is generally conducted under conditions of agitation and in the presence of an inert liquid diluent such as n-hexane, n-heptane, carbon tetrachloride and diethylether. The nitroketone can then be recovered if desired by standard recovery procedures, for example by filtration of the solids after the addition of the reaction mixture to water or by distillation. The nitroketone is converted to the ammonium, Group IA metal or Group IIA metal salt by contacting with from about 1 to about 10 moles of ammonia, a Group IA metal hydroxide or a Group IIA metal oxide or hydroxide per mole of nitroketone at a temperature of about −10° to 30° C.

In one embodiment there is contemplated heating the salt of the nitroketone as heretofore described at a temperature of from about 60° to 200° C., preferably from about 75° to 130° C. with an acidic mineral acid salt in the presence of a monocarboxylic acid as solvent. Acidic mineral acid salts contemplated herein include the ammonium chloride, ammonium nitrate, ammonium sulfate, ammonium hydrogen sulfate, ammonium phosphate, aluminum nitrate, ferric chloride, cupric nitrate, zinc sulfate and calcium nitrate. The acidic salts mentioned above form a group which enable the method to form the desired carboxylic and hydroxamic acids. Other acidic mineral acid salts such as calcium chloride and calcium sulfate do not function in the same manner and fail to provide as reaction products the desired carboxylic and hydroxamic acids. In particularly preferred embodiments there is employed as the acidic mineral acid salt ammonium nitrate or calcium nitrate. The mole ratio of the nitroketone salt to acidic mineral acid salt employed herein can range from about 1:0.01 to 1:2 and preferably from about 1:0.1 to 1:1. Further, the reaction described above can be conducted under substantially anhydrous conditions and it is generally preferred that the water content in the reaction be maintained below about three weight percent as the same is beneficial in preventing hydrolysis of the hydroxamic acid to a carboxylic acid.

As provided herein, the reaction involving cleavage and reaction of the salt of the nitroketone to the corresponding carboxylic and hydroxamic acids is conducted in the presence of a monocarboxylic acid solvent suitably having from 1 to 16 carbon atoms, as for example formic acid, acetic acid, propionic acid, isobutanoic acid, pentanoic acid, hexanoic acid, octanoic acid, decanoic acid, undecanoic acid, dodecanoic acid and hexadecanoic acid and preferably a carboxylic acid having from 1 to 6 carbon atoms such as formic, acetic or propionic acids is employed. A particularly preferred acid is acetic acid. The carboxylic acid solvent assists in solubilizing the salt of the nitroketone thereby insuring good contact between the reactants. Usually, the carboxylic acid solvent is employed in the instant method in a mole ratio of nitroketone salt to solvent of about 1:1 to 1:100, preferably about 1:4 to 1:40. The presence of the solvent in the course of the reaction contributes to the improved yields of acid products and permits the reaction to be substantially completed in about one-quarter to 3 hours although longer reaction time may be employed.

Upon completion of the reaction and the formation of the desired products, the carboxylic and hydroxamic acids can be recovered by extraction with an inert organic solvent followed by stripping the solvent. Any organic solvent which does not react with the acids and in which the acids are soluble can be employed. Preferably the solvent possesses a boiling point of between 30° and 120° C. as for example ethyl ether, benzene, n-hexane, n-heptane, and carbon tetrachloride.

In a highly preferred embodiment of this invention there is contemplated a method for preparing a carboxylic acid and a hydroxamic acid wherein an internally unsaturated olefin as described above is nitrooxidized and contacted with a denitrating agent to form a crude composition comprising a mixture of the nitroketone and denitrating agent along with by-products, nitric acid and the corresponding nitronitrate and nitroalcohol. This crude composition is subsequently contacted with about 2 to about 10, preferably 2 to 2.5 moles of ammonia, a Group IA metal hydroxide or a Group IIA metal oxide or hydroxide per mole of nitroketone at a temperature of about −10° to 30° C. In the course of contacting the crude composition with the basic material, such as ammonia or calcium oxide, nitric acid is converted to the corresponding nitrate salt, such as ammonium nitrate or calcium nitrate, and the nitroketone is converted to its salt, such as the ammonium or calcium salt of the nitroketone. The salts of the nitroketone and nitric acid are both insoluble in the crude composition and can be easily separated therefrom as by filtration, centrifugation, decantation, etc. The filtrate, is separate from the insoluble salts, comprises the denitrating agent and by-products, nitronitrates and nitroalcohols, each of which are soluble and do not react with ammonia or calcium oxide. There is then introduced to the salts of the nitroketone and nitric acid, a monocarboxylic acid of the type described above in an amount of about 1 to 100 moles, preferably 4 to 40 moles of carboxylic acid per mole of nitroketone salt and the reaction mixture is heated as previously described, thereby cleaving and converting the nitroketone salt to the corresponding carboxylic and hydroxamic acids.

By the instant method, salts of nitroketones can be converted to the corresponding carboxylic and hydroxamic acids at high conversion and selectivities. The acids, so prepared by the instant method, are useful as chemical intermediates and intermediates in the synthesis of fuels and lubricant additives.

In order to more fully illustrate the nature of this invention and the manner of practicing the same the following examples are presented.

EXAMPLE I

Into a 200 milliliter flask equipped with a gas inlet thermometer and condenser, there was charged 11.9 grams (0.05 mole) of 7-heptadecene, 3.65 grams (.05 mole) of dimethyl formamide and 80 milliliters of carbon tetrachloride. To this solution, maintained at a temperature of 5°–10° C., there was introduced oxygen at the rate of 60 to 80 milliliters per minute and 4.6 grams (0.05 mole) of dinitrogen tetroxide at the rate of 0.5 gram per minute over a period of one hour.

To the above reaction mixture, maintained at 5°–10° C., there was introduced 1.70 gram (.10 mole) of ammonia as a gas at the rate of 0.06 gram per minute over a period of one-half hour. The solids composed of ammonium nitrate and the ammonium salts 7-nitro-8-heptadecanone and 8-nitro-7-heptadecanone were separated from the crude composition by filtration and weighed 19.0 grams. To the solids, there was added 150 milliliters of acetic acid and the mixture was heated at 118° C. for three hours. The solution was cooled to room temperature, 300 milliliters of water added thereto, extracted with three 100 milliliter portions of ether, dried and stripped. The recovered residue weighing 13.2 grams (84 percent yield) was identified by infrared and nuclear magnetic resonance to be n-nonanoic acid, n-octanoic acid, n-octanohydroxamic acid and n-nonanohydroxamic acid.

EXAMPLE II

To the apparatus of Example I was charged 11.9 grams of 7-heptadecene, 3.65 grams of dimethyl formamide in 80 milliliters of carbon tetrachloride and the solution treated with oxygen and dinitrogen tetroxide as in Example I.

At the end of the dinitrogen tetroxide-oxygen addition period, 2.8 grams (0.05 mole) of calcium oxide was added to the reaction mixture maintained at 5°–10° C. After stirring for 15 minutes, the solids, calcium salt of the nitroketone and calcium nitrate were seperated by filtration and weighed 20.5 grams. To the solids there was added 150 milliliters of acetic acid and the mixture was heated to 118° C. for 3 hours. The solution was cooled to room temperature, 300 milliliters of water added thereto, extracted three times with 100 milliliter portions of ether, dried and stripped. The recovered residue weighed 13.2 grams (84 percent yield) was identified by infrared and nuclear magnetic resonance spectroscopy to be n-nonanoic acid, n-octanoic acid, n-octanohydroxamic acid and n-nonanohydroxamic acid.

EXAMPLE III

Employing the apparatus and procedure of Example I, there was charged 5.6 grams (.05 mole) of 4-octene along with dimethyl formamide, carbon tetrachloride, oxygen, dinitrogen tetroxide, ammonia and acetic acid. After work up as in Example I, 7.35 grams (85 percent yield) of residue was recovered and was identified as n-butyric acid and n-butyrohydroxamic acid.

I claim:

1. A method of preparing a carboxylic acid a hydroxamic acid which comprises contacting an ammonium, Group IA or Group IIA metal salt of an internal nitroketone corresponding to the formula:

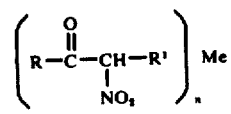

where R and R¹ are alkyl groups having from 1 to 25 carbon atoms, where Me is $NH_4$, a Group IA metal or a Group IIA metal and where n is 1 or 2, with an acidic mineral acid salt, wherein said acidic salt is ammonium chloride, ammonium nitrate, ammonium sulfate, ammonium hydrogen sulfate, ammonium phosphate, aluminum nitrate, aluminum sulfate, ferric chloride, cupric nitrate, zinc sulfate or calcium nitrate in the presence of a carboxylic acid solvent under substantially anhydrous conditions at a temperature of about 60 to 200° C. wherein the mole ratio of said nitroketone salt to said acidic salt is from about 1:0.01 to 1:2.

2. A method according to claim 1 wherein said containing is at a temperature of about 75° to 130° C.

3. A method according to claim 1 where the mole ratio of said nitroketone salt to said acidic salt is from about 1:0.1 to 1:1.

4. A method according to claim 1 wherein said nitroketone salt is ammonium 7-nitro-8-heptadecanone.

5. A method according to claim 1 wherein said nitroketone salt is ammonium 8-nitro-7-heptadecanone.

6. A method according to claim 1 wherein said nitroketone salt is ammonium 5-nitro-4-octanone.

7. A method according to claim 1 wherein said nitroketone salt is calcium 7-nitro-8-heptadecanone.

8. A method according to claim 1 wherein said nitroketone salt is calcium 5-nitro-4-octanone.

9. A method according to claim 1 wherein said carboxylic acid has from 1 to 16 carbon atoms.

10. A method according to claim 1 wherein said carboxylic acid has from 1 to 6 carbon atoms.

11. A method according to claim 1 wherein said carboxylic acid is acetic acid.

12. A method according to claim 1 wherein said acidic salt is ammonium nitrate.

13. A method according to claim 1 wherein said acid salt is ammonium sulfate.

14. A method according to claim 1 wherein said acid salt is ammonium chloride.

15. A method according to claim 1 wherein said acid salt is ammonium phosphate.

16. A method according to claim 1 wherein said acid salt is calcium nitrate.

* * * * *

UNITED STATES PATENT AND TRADEMARK OFFICE
CERTIFICATE OF CORRECTION

PATENT NO. : 4,000,171
DATED : December 28, 1976
INVENTOR(S) : Mahmoud S. Kablaoui It is certified that error appears in the above-identified patent and that said Letters Patent are hereby corrected as shown below:

Claim 1, Line 1   "acid a" should read "acid and a"

Claim 2, Lines 1-2   "said containing is' should read "said contacting is"

Signed and Sealed this

Sixteenth Day of October 1979

[SEAL]

Attest:

RUTH C. MASON
*Attesting Officer*

LUTRELLE F. PARKER
*Acting Commissioner of Patents and Trademarks*